(12) United States Patent
Laeuger et al.

(10) Patent No.: US 11,987,539 B2
(45) Date of Patent: May 21, 2024

(54) DICARBOXYLIC ACID DIESTERS

(71) Applicant: DSM IP ASSETS B.V., Heerlen (NL)

(72) Inventors: Stefan Karl Laeuger, Kaiseraugst (CH); Ulla Letinois, Kaiseraugst (CH); Peter Riebel, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 800 days.

(21) Appl. No.: 17/047,883

(22) PCT Filed: Apr. 23, 2019

(86) PCT No.: PCT/EP2019/060344
§ 371 (c)(1),
(2) Date: Oct. 15, 2020

(87) PCT Pub. No.: WO2019/206892
PCT Pub. Date: Oct. 31, 2019

(65) Prior Publication Data
US 2021/0163397 A1 Jun. 3, 2021

(30) Foreign Application Priority Data

Apr. 25, 2018 (EP) .................................. 18169247

(51) Int. Cl.
| | | |
|---|---|---|
| *C07C 203/04* | (2006.01) | |
| *A23K 20/105* | (2016.01) | |
| *A23K 20/158* | (2016.01) | |
| *A23K 50/10* | (2016.01) | |

(52) U.S. Cl.
CPC .......... *C07C 203/04* (2013.01); *A23K 20/105* (2016.05); *A23K 20/158* (2016.05); *A23K 50/10* (2016.05)

(58) Field of Classification Search
CPC ................................................... C07C 203/04
See application file for complete search history.

(56) References Cited

FOREIGN PATENT DOCUMENTS

| | | |
|---|---|---|
| WO | 2011/070133 | 6/2011 |
| WO | 2012/084629 | 6/2012 |

OTHER PUBLICATIONS

PubChem CID 90798906, National Center for Biotechnology Information. PubChem Compound Summary for CID 90798906, Bis(3-nitrooxypropyl) butanedioate. https://pubchem.ncbi.nlm.nih.gov/compound/Bis_3-nitrooxypropyl_-butanedioate. Accessed Jul. 13, 2023, create date Mar. 16, 2015. (Year: 2015).*
PubChem CID 87666717, National Center for Biotechnology Information. PubChem Compound Summary for CID 87666717, Bis(2-nitrooxyethyl) butanedioate. https://pubchem.ncbi.nlm.nih.gov/compound/Bis_2-nitrooxyethyl_-butanedioate. Accessed Sep. 26, 2023, create date Feb. 12, 2015. (Year: 2015).*
International Search Report for PCT/EP2019/060344 dated Jul. 8, 2019, 3 pages.
Written Opinion of the ISA for PCT/EP2019/060344 dated Jul. 8, 2019, 5 pages.
CAS Registry No. 1404066-04-1, Nov. 16, 2012.

* cited by examiner

*Primary Examiner* — Laura L Stockton
(74) *Attorney, Agent, or Firm* — NIXON & VANDERHYE P.C.

(57) ABSTRACT

The present invention relates to novel dicarboxylic diesters as well as the use thereof as for inhibiting the methane production in ruminants.

9 Claims, No Drawings

DICARBOXYLIC ACID DIESTERS

This application is the U.S. national phase of International Application No. PCT/EP2019/060344 filed Apr. 23, 2019 which designated the U.S. and claims priority to EP Patent Application No. 18169247.6 filed Apr. 25, 2018.

The present invention relates to novel dicarboxylic acid diesters as well as the use thereof as for inhibiting the methane production in ruminants.

The temperature of the air surrounding the earth is increasing, a process referred to as global warming. One of the main focuses to reduce this warming effect is to reduce the amount of greenhouse gases emitted into the atmosphere. Greenhouse gases are emitted from several different sources, both natural and artificial; however, the two sources with the most emphasis are the agricultural and fossil fuel industries. Within agriculture, ruminants and in particular cattle are the major contributors to the biogenic methane formation, and it has been estimated that the prevention of methane formation from ruminants would almost stabilize atmospheric methane concentrations.

Methane emission from the ruminant livestock sector—a by-product from enteric fermentation of plant biomass in the ruminant digestive system—is produced by methanogenic archaea. Various attempts have been made in the last decade to mitigate methane production from ruminant animals. Although the approaches vary, the most popular method so far are feed additives which act in the rumen fluid by reducing respectively inhibiting the methane production by methanogenic archaea. It has, however, been found that the many methane reducing agents such as e.g. 3-nitrooxypropanol have a relatively high vapor pressure which makes it extremely storage instable, i.e. the active is readily lost upon storage. Consequently, the methane inhibiting agent generally has to be overdosed, which is not desirable.

Thus, there is an ongoing need for methane inhibiting agent, which exhibit an efficient methane reducing effect. Furthermore, such compounds should exhibit a low vapor pressure at 20° C. (i.e. a vapour pressure of less than 0.01 mbar) to enhance the storage stability thereof.

Surprisingly, it has now been found that certain novel dicarboxylic acid diesters are able to effectively inhibit the methane formation in the rumen fluid, while exhibiting very low vapor pressures, which renders them more storage stable.

Thus, in a first embodiment, the present invention relates to dicarboxylic acid diesters of formula (I)

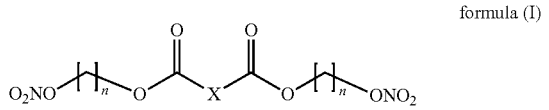

formula (I)

wherein
n is an integer selected in the range from 1 to 15, and
X is a $C_{1-24}$-alkylene group, a $C_{2-24}$-alkenylene group or a $C_{6-24}$-arylene group, with the proviso that when n is >3 the resulting hydrocarbon chain may be interrupted by —O— or —NH—.

In a preferred embodiment, the present invention relates to dicarboxylic diester of formula (I), wherein n is an integer selected in the range from 1 to 15, and X is a $C_{1-24}$-alkylene group, a $C_{2-24}$-alkenylene group or a $C_{6-24}$-arylene group.

The term $C_{1-24}$-alkylene group refers to linear $C_{1-24}$-alkylene group or cyclic $C_{3-24}$-alkylene groups having from 1, respectively 3 to 24 carbon atoms which may optionally be substituted with a $C_1$-$C_{26}$-alkyl group at any carbon atom. Said $C_1$-$C_{26}$-alkyl substituent is preferably chosen from the group of methyl, octenyl, nonenyl, decenyl, undecenyl or dodecenyl. Preferred $C_{1-24}$-alkylene groups in all embodiments of the present invention are linear (unsubstituted) $C_{1-24}$-alkylene groups (i.e. *—$(CH_2)_m$—*), wherein m is an integer selected in the range from 1 to 24 as well as unsubstituted cyclic $C_{3-6}$-alkylene groups such as ethylene, ethylene, propylene, butylene, pentylene, hexylene, 1,2-cyclopentylene, 1,2-cyclohexylene and 1,4-cyclohexylene without being limited thereto. Particularly preferred $C_{1-24}$-alkylene groups in all embodiments of the present invention are linear (unsubstituted) $C_{1-10}$-alkylene groups, even more preferred are linear (unsubstituted) $C_{1-5}$-alkylene groups such as in particular methylene, ethylene and propylene.

The term $C_{2-24}$-alkenylene group as used herein refers to linear $C_{2-24}$-alkyl or cyclic $C_{3-24}$-alkyl groups having from 2 respectively 3 to 24 carbon atoms which have at least one carbon-carbon double bond, which can independently of each other be in (E) or (Z) configuration, and which may optionally be substituted by an alkyl group as defined above at any carbon atom such as e.g. vinylene (ethenylene), propenylene, butenylene and cyclohexenylene without being limited thereto. Preferred $C_{2-24}$-alkenylene groups in all embodiments of the present invention are linear $C_{2-24}$-alkenylene groups, i.e. *—$(CH_2)_o$—(CH=CH)$_p$—$(CH_2)_q$—* diradicals, wherein o is an integer selected in the range from 0 to 22, p is an integer selected in the range from 1 to 12 and q is an integer selected in the range from 0 to 22. A particularly preferred $C_{2-24}$-alkenylene group in all embodiments of the present invention is vinylene (in (E) or (Z)-configuration).

The term $C_{6-24}$-arylene group refers to aromatic aryldiradicals which may optionally be substituted by an alkyl group atom as defined above at any carbon atom. Preferably, in all embodiments of the present invention, the $C_{6-24}$-arylene groups are unsubstituted or substituted by one methyl group. Particularly preferred in all embodiments of the present invention are $C_{6-10}$-arylene groups such as in particular 1,2-phenylene, 1,3-phenylene, 1,4-phenylene, (methyl)-1,2-phenylene and 2,6-naphthylene.

In all embodiments of the present invention n is preferably selected in the range from 3 to 9, more preferably in the range from 3 to 6. Most preferably in all embodiments of the present invention n is 3.

In all embodiments of the present invention X is preferably selected from the group of a $C_{1-10}$-alkylene group, a $C_{2-5}$-alkenylene group and a $C_{6-10}$-arylene group, more preferably from the group of an unsubstituted $C_{1-10}$-alkylene group, an unsubstituted $C_{2-5}$-alkenylene group and an unsubstituted $C_{6-10}$-arylene group, most preferably from the group of an unsubstituted $C_{1-5}$-alkylene group, an unsubstituted $C_{2-4}$-alkenylene group, 1,2-phenylene, 1,3-phenylene and 1,4-phenylene such as in particular from the group of an unsubstituted $C_{1-3}$-alkylene group and vinylene (i.e. *—(CH=CH)—*)). It is furthermore preferred if said alkylene respectively alkenylene groups are linear alkylene respectively alkenylene groups.

Particularly advantageous dicarboxylic diester of formula (I) are listed in table 1.

TABLE 1

| Structure | Formula |
|---|---|
| 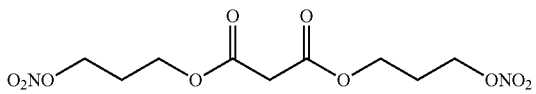 bis(3-(nitrooxy)propyl) malonate | (I-a) |
| 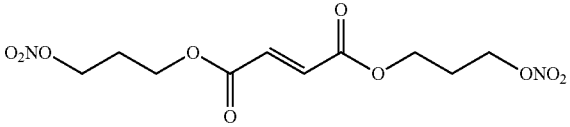 bis(3-(nitrooxy)propyl) fumarate | (I-b) |
| 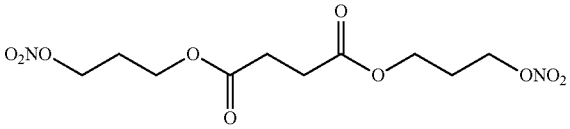 bis(3-(nitrooxy)propyl) succinate | (I-c) |

The compounds of the present invention can be manufactured according to standard methods in the art known for the preparation of nitrooxy organic molecules as well as esters. The nitrooxy group may e.g. be introduced in a reaction of the respective alcohol with nitrosulfuric acid. The diesters may e.g. be prepared by esterification of the respective dicarboxylic acids respectively the corresponding acid chlorides or (cyclic) anhydrides thereof with a nitrooxyalkanol or a diol.

Thus, the present invention also relates to a process for the manufacture of a diester of formula (I), said process encompassing the step of reacting a dicarboxylic acid of formula (II), respectively an acid chloride or a (cyclic) anhydride thereof, with a nitrooxyalcohol of formula (III).

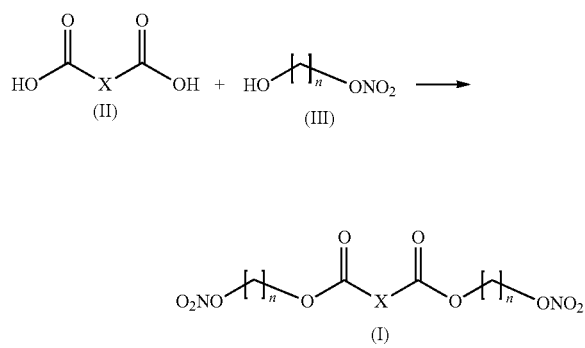

Alternatively, in a first step the fatty acid can be reacted with the respective diol to form a monoester, followed by reacting the respective monoester with nitrosulfuric acid.

Thus, in another embodiment, the present invention relates to a process for the manufacture of a dicarboxylic diester of formula (I), said process encompassing the step of reacting a fatty acid of formula (II), respectively an acid chloride or a (cyclic) anhydride thereof, with an alcohol of formula (IV), followed by reacting the obtained fatty acid monoester (V) with nitrosulfuric acid to the diester of formula (I).

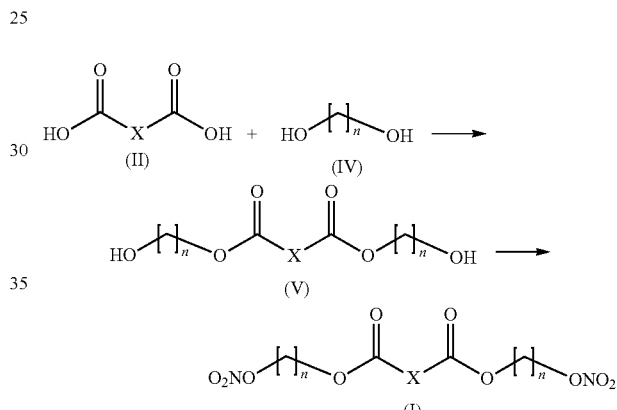

It is well understood, that all the definitions and preferences as given herein also apply to the process according to the present invention.

Examples of suitable dicarboxylic acids include linear saturated dicarboxylic acids such as in particular malonic acid, succinic acid, glutaric acid, adipic acid, pimelic acid, suberic acid, azelaic acid and sebacic acid, unsaturated dicarboxylic acids such as in particular maleic acid, fumaric acid, glutaconic acid and mesaconic acid, cyclic saturated dicarboxylic acids such as 1,2-cyclopentanedicarboxylic acid, 1,2-dicyclohexanedicarboxylic acid and cyclic unsaturated dicarboxylic acids such as trans-4-cyclohexene-1,2-dicarboxylic acid, as well as aromatic dicarboxylic acids such as in particular phthalic acid, isophthalic acid, terephthalic acid and 2,6-naphthalenedicarboxylic acid.

Examples of suitable cyclic anhydrides include phthalic anhydride, tetrahydrophthalic anhydride, naphtalenic dicarboxylic anhydride, hexahydrophthalic anhydride, 5-norbornene-2,3dicarboxylic anhydride, norbornene-2,3-dicarboxylic anhydride, naphtalenic dicarboxylic anhydride, 2-dodecene-1-yl-succinic anhydride, maleic anhydride, trimellitic anhydride, (methyl, octyl or dodecenyl) succinic anhydride, glutaric anhydride, 4methylphthalic anhydride, 4-methylhexahydrophthalic anhydride and 4-methyltetrahydrophthalic anhydride.

Preferred dicarboxylic acids in the processes according to the present invention are selected from the group of malonic acid, maleic acid, fumaric acid, succinic acid and glutaric acid, most preferably from the group of malonic acid, succinic acid and fumaric acid.

The most preferred alcohol of formula (III) respectively the diol of formula (IV) in the processes according to the present invention are 3-nitrooxypropanol respectively 1,3-propandiol.

In a further embodiment the present invention relates to the use of at least one dicarboxylic diester as defined by formula (I) and with all the definitions and preferences as given herein as an active compound in animal feeding for reducing the formation of methane emanating from the digestive activities of ruminants and/or for improving ruminant performance.

The invention further provides a method for reducing the production of methane emanating from the digestive activities of ruminants and/or for improving ruminant animal performance, said method comprising orally administering a sufficient amount of at least one dicarboxylic diester as defined by formula (I) with all the definitions and preferences as given herein to the animal. It is to be understood by oral administration a simple feeding, or manual administration of a bolus.

The dicarboxylic acid diesters according to the present invention are particularly suitable to act over an extended period of time, i.e. over a period of at least 10 hours, preferably at least 16 hours, most preferably at least 20 such as a period of 24 hours after administration.

Thus, the present invention also relates to uses or methods according to the present invention, wherein the doses are separated in time from each other by at least 10 hours, preferably by at least 16 hours, more preferably by at least 20 hours, most preferably by at least 24 hours.

Ruminating mammals according to the present invention include cattle, goats, sheep, vgiraffes, American Bison, European bison, yaks, water buffalo, deer, camels, alpacas, llamas, wildebeest, antelope, pronghorn, and nilgai.

For all embodiments of the present invention, domestic cattle, sheep and goat are the more preferred species. For the present purposes the most preferred species are domestic cattle. The term includes all races of domestic cattle, and all production kinds of cattle, in particular dairy cows and beef cattle.

The present invention also relates to the use of at least one dicarboxylic diester as defined by formula (I) and with all the definitions and preferences as given herein, wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the volatile fatty acids (VFA) profile in milk.

The present invention also relates to the use at least one dicarboxylic diester as defined by formula (I) and with all the definitions and preferences as given herein, wherein the amount of the at least one dicarboxylic diester administered to the ruminant animal is selected in the range from 1 mg to 10 g per kg of feed, preferably from 10 mg to 1 g per kg of feed, more preferably, from 50 mg to 500 mg per kg of feed.

As indicated above, the dicarboxylic diesters of the present invention are useful as compounds for feed additives and animal feed compositions for ruminants, and accordingly are useful as the active ingredients in such feed to reduce methane formation in the digestive tract of the animal, and/or to improve ruminant performance.

For the realisation of their use as such ingredients for the feed of ruminants the at least one dicarboxylic diester as defined by formula (I) with all the definitions and preferences as given herein may be incorporated in the feed by methods known per se in the art of feed formulation and processing.

Further aspects of the present invention are therefore formulations, i.e. feed additives and animal feed compositions containing at least one dicarboxylic diester as defined by formula (I) with all the definitions and preferences as given herein.

The present invention therefore also relates to a feed composition or a feed additive comprising at least one dicarboxylic diester as defined by formula (I) and with all the definitions and preferences as given herein. Preferably, the feed composition or feed additive is a ruminant base mix. In a preferred embodiment, the composition is a mineral premix, a vitamin premix including vitamins and minerals or a bolus.

The normal daily dosage of a dicarboxylic diester according to the invention provided to an animal by feed intake depends upon the kind of animal and its condition. Normally this dosage should be in the range of from about 1 mg to about 10 g, preferably from about 10 mg to about 1 g, more preferably, 50 mg to 500 mg compound per kg of feed.

The at least one dicarboxylic diester as defined by formula (I) and with all the definitions and preferences as given herein may be used in combination with conventional ingredients present in an animal feed composition (diet) such as calcium carbonates, electrolytes such as ammonium chloride, proteins such as soya bean meal, wheat, starch, sunflower meal, corn, meat and bone meal, amino acids, animal fat, vitamins and trace minerals.

Particular examples of compositions of the invention are the following:
   An animal feed additive comprising (a) at least one compound selected from table 1 and (b) at least one fat-soluble vitamin, (c) at least one water-soluble vitamin, (d) at least one trace mineral, and/or (e) at least one macro mineral;
   An animal feed composition comprising at least one compound selected from table 1 and a crude protein content of 50 to 800 g/kg feed.

Therefore, in a preferred embodiment, the present invention relates to a ruminant feed composition or feed additive The so-called premixes are examples of animal feed additives of the invention. A premix designates a preferably uniform mixture of one or more micro-ingredients with diluents and/or carrier. Premixes are used to facilitate uniform dispersion of micro-ingredients in a larger mix.

Apart from the dicarboxylic diesters of the invention, the premix of the invention preferably contains at least one fat-soluble vitamin, and/or at least one water soluble vitamin, and/or at least one trace mineral, and/or at least one macro mineral. In other words, the premix of the invention comprises the at least one compound according to the invention together with at least one additional component selected from the group consisting of fat-soluble vitamins, water-soluble vitamins, trace minerals, and macro minerals.

Macro minerals may be separately added to the feed. Therefore, in a particular embodiment, the premix comprises the dicarboxylic diesters of the invention together with at least one additional component selected from the group consisting of fat-soluble vitamins, water-soluble vitamins, and trace-minerals.

The following are non-exclusive lists of examples of these components:
- Examples of fat-soluble vitamins are vitamin A, vitamin D3, vitamin E, and vitamin K, e.g. vitamin K3.
- Examples of water-soluble vitamins are vitamin B12, biotin and choline, vitamin B1, vitamin B2, vitamin B6, niacin, folic acid and panthothenate, e.g. Ca-D-panthothenate.
- Examples of trace minerals are manganese, zinc, iron, copper, iodine, selenium, and cobalt.
- Examples of macro minerals are calcium, phosphorus and sodium.

As regards feed compositions for ruminants such as cows, as well as ingredients thereof, the ruminant diet is usually composed of an easily degradable fraction (named concentrate) and a fiber-rich less readily degradable fraction (named hay, forage, or roughage).

Hay is made of dried grass, legume or whole cereals. Grasses include among others timothy, ryegrasses, fescues. Legumes include among others clover, lucerne or alfalfa, peas, beans and vetches. Whole cereals include among others barley, maize (corn), oat, sorghum. Other forage crops include sugarcane, kales, rapes, and cabbages. Also root crops such as turnips, swedes, mangles, fodder beet, and sugar beet (including sugar beet pulp and beet molasses) are used to feed ruminants. Still further crops are tubers such as potatoes, cassava and sweet potato. Silage is an ensiled version of the fiber-rich fraction (e.g. from grasses, legumes or whole cereals) whereby material with a high water content is treated with a controlled anaerobic fermentation process (naturally-fermented or additive treated).

Concentrate is largely made up of cereals (such as barley including brewers grain and distillers grain, maize, wheat, sorghum), but also often contain protein-rich feed ingredients such as soybean, rapeseed, palm kernel, cotton seed and sunflower.

Cows may also be fed total mixed rations (TMR), where all the dietary components, e.g. forage, silage and concentrate, are mixed before serving.

As mentioned above a premix is an example of a feed additive which may comprise the at least one dicarboxylic diester as defined by formula (I) and with all the definitions and preferences as given herein. It is understood that the dicarboxylic diester according to the present invention may be administered to the animal in different other forms. For example, the dicarboxylic diesters can also be included in a bolus that would be placed in the rumen and that would release a defined amount of the dicarboxylic diester continuously in well-defined dosages over a specific period of time.

The present invention further relates to a method for reducing the production of methane emanating from the digestive activities of ruminants and/or for improving ruminant animal performance, comprising the oral administration of a sufficient amount of at least one the dicarboxylic diester as defined by formula (I) and with all the definitions and preferences as given herein.

Moreover, the invention further relates to a method as described above, wherein the dicarboxylic diester of formula (I) is administered to the animal in combination with at least one additional active substance selected from the group consisting of diallyl disulfide, garlic oil, allyl isothiocyanate, deoxycholic acid, chenodeoxycholic acid and derivatives thereof.

The invention also relates to a method as described above, wherein the ruminant animal is selected from the group consisting of: cattle, goats, sheep, giraffes, American Bison, European bison, yaks, water buffalo, deer, camels, alpacas, llamas, wildebeest, antelope, pronghorn, and nilgai, and more preferably from the group consisting of: cattle, goats and sheep.

The invention also relates to a method as described above, wherein the amount of the at least one dicarboxylic diester as defined in formula (I) and with all the definitions and preferences as given herein administered to the ruminant animal is from about 1 mg to about 10 g per kg feed, preferably from about 10 mg to about 1 g, more preferably from 50 mg to 500 mg compound per kg of feed.

The invention also relates to a method as described above, wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The invention also relates to a method as described above, wherein the ruminant feed conversion ratio is reduced by at least 1% when measured in conventional performance trial. Preferably, the feed conversion ratio is reduced by at least 2%, more preferably, by at least 2.5%, even more preferably, by at least 3%, most preferably, by at least 3.5%.

The present invention is further described by the following examples which should not be construed as limiting the scope of the invention.

EXAMPLE 1: SYNTHESIS OF 3-NITROOXY-PROPYL DIESTERS a.) Preparation of bis(3-(nitrooxy)propyl) malonate (I-a)

12.7 g 3-nitrooxypropanol, 60 ml methylenchloride and 6.2 ml triethylamine are placed in a three-necked round bottom flask and the clear solution is cooled to 0° C. 7.3 g malonylchlorid is dissolved in 10 ml dichloromethane, transferred to the dropping funnel and added dropwise to the 3-nitrooxypropanol solution over 15 minutes, Gas formation is observed. The temperature rose to 28° C. After finishing the addition, the mixture is left stirring for 20 hours at room temperature. Then 5 g anhydrous potassium carbonate is added (002-formation) and the orange suspension is stirred for 30 minutes. The solids are filtered off and washed with 20 mL of dichloromethane. The clear, orange filtrate is concentrated under reduced pressure (10 mbar, 40° C. bath temperature). The product is obtained in 15.6 g as orange oil. The crude product was purified by dilution in 50 ml methyl tert-butylether (MTBE) and washed ten times with 50 ml of water, dried over sodium sulfate and concentrated under reduced pressure. The pure product was obtained in 14.2 g in (purity: 93%; vapor pressure: 0.00133 mbar)

b.) Preparation of bis(3-(nitrooxy)propyl) fumarate (I-b)

4.89 g 3-nitrooxypropanol, 24.3 ml methylenchlorid and 6.2 ml triethylamine are placed in a three-necked round bottom flask and the clear solution is cooled to 0° C. Fumarylchloride (2.28 ml) is dissolved in 10 ml dichloromethane, transferred to the dropping funnel and added dropwise to the 3-nitrooxypropanol solution over 15 minutes, keeping the temperature below 5° C. The color changes immediately to dark brown. In the end the mixture is allowed to warm to 24° C. and left stirring for four hours. Then the viscous reaction mixture is diluted with 200 ml ethyl acetate and extracted with 200 ml 2N hydrochloric acid. The aqueous phase is then re-extracted with 100 ml ethyl acetate and the combined organic phases washed three times with 200 mL water each (total 600 mL). The organic phase is dried over sodium sulfate and concentrated under reduced pressure (40° C./<0.1 mbar). The product is obtained in 5.2 g as dark-brown oil. The crude product was purified by column chromatography (120 g SiO2-column, eluent cyclohexane with 30% MTBE). The pure product was obtained in 2.32 g (purity: 96%; vapor pressure 0.00133 mbar)

c.) Preparation of bis(3-(nitrooxy)propyl) succinate (I-c)

5.14 g of 3-nitrooxypropanol was dissolved in 20 ml dichloromethane and 2.319 ml succinyl dichloride was added. The mixture was stirred at 23° C. for 16 hours. Solid potassium carbonate was added until no further evolution of carbon dioxide was visible, then the mixture was filtered, the filter residue washed with acetone and the filtrate was concentrated under reduced pressure yielding 6.35 g of a nearly colorless liquid. The crude product was dissolved in 50 ml t-butylmethylether and washed 10 times with water (50 ml each). The organic phase was dried with magnesium sulfate and evaporated under reduced pressure yielding 5.7 g of bis(3-(nitrooxy)propyl) succinate (yield: 83%; purity: 94.7%, vapor pressure: 0.00133 mbar).

EXAMPLE 2: IN VITRO TEST FOR METHANE PRODUCTION

A modified version of the "Hohenheim Forage value Test (HFT)" was used for testing the effect of specific compounds on the rumen functions mimicked by this in-vitro system.

Principle: Feed (i.e. a TMR) (300 mg) is given into a syringe with a composition of rumen liquor and an appropriate mixture of buffers (i.e. rumen-fluid buffer mix: 25 ml) and the substances to be tested in the concentrations as outlined in table 2 (the inhibitors to be tested are diluted in ethanol to reach the respective concentration of dry matter in 50 µl). The solution is incubated at 39° C. for 8 h. The quantity of produced gas is measured and put into a formula for conversion. After the incubation the composition of gas is measured with a GC.

Reagents:
Mass Element Solution:
6.2 g potassium dihydrogen phosphate ($KH_2PO_4$)
0.6 g magnesium sulfate heptahydrate ($MgSO_4*7H_2O$)
9 ml concentrated phosphoric acid (1 mol/l)
dissolved in distilled water to 1 l (pH about 1.6)
Buffer Solution:
35.0 g sodium hydrogen carbonate ($NaHCO_3$)
4.0 g ammonium hydrogen carbonate (($NH_4$)$HCO_3$)
dissolved in distilled water to 1 l Trace Element Solution:
13.2 g calcium chloride dihydrate ($CaCl_2*2H_2O$)
10.0 g manganese(II) chloride tetrahydrate ($MnCl_2*4H_2O$)
1.0 g cobalt(II) chloride hexahydrate ($CoCl_2*6H_2O$)
8.0 g iron(III) chloride ($FeCl_3*6H_2O$)
dissolved in distilled water to 100 ml
Sodium Salt Solution:
100 mg sodium salt
dissolved in distilled water to 100 ml
Reduction Solution:
first 3 ml sodium hydroxide (c=1 mol/l), then 427.5 mg sodium sulfide hydrate ($Na_2S*H_2O$) are added to 71.25 ml $H_2O$
solution must be prepared shortly before it is added to the medium solution Procedure:
Sample Weighing:
TMR (44% concentrate, 6% hay, 37% maize silage and 13% grass silage) is sieved to 1 mm and weighed exactly into the syringes. One run contains 4 repetitions, each with 16 syringes and comprises substrate controls, which display the gas production without the effect of the tested compounds, carrier controls, which display the gas production in the presence of the carrier (solvent) only (i.e. EtOH used to dissolve the test compounds), and test samples (in the carrier), which contain the test substances in varying concentrations as outlined in table 2.

Preparation of the Rumen-Fluid-Buffer-Mix (Medium Solution):
The components are mixed in a Woulff bottle in following order:
711 ml water
0.18 ml trace element solution
355.5 ml buffer solution
355.5 ml mass element solution
The completed solution is warmed up to 39° C. followed by the addition of 1.83 ml sodium salt solution and the addition of reduction solution at 36° C.

The rumen liquor (750 ml) is added, when the indicator turns colorless under continued agitation and 002-gassing.

Filling the syringes, incubation and determining gas volumes:

The rumen-fluid-buffer-mix is added to the glass syringe prepared as outlined above containing the TMR and the active to be tested. The syringes are then incubated for 8 hours at 39° C. under gentle agitation. After 8 the volume of gas produced is measured, and the percentage of methane in the gas phase is determined by gas chromatography.

Results

Table 2 outlines the methane inhibiting effect of various dicarboxylic acid diesters according to the present invention at different concentrations.

TABLE 2

| | | Methane inhibition* | | |
|---|---|---|---|---|
| # | Structure | 10 µmol/l | 5 µmol/l | 2.5 µmol/l |
| (I-a) | 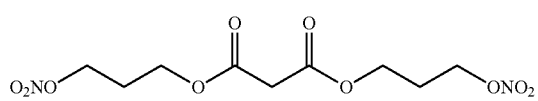<br>bis(3-(nitrooxy)propyl) malonate | −99 | −97 | −72 |

TABLE 2-continued

| # | Structure | Methane inhibition* | | |
|---|---|---|---|---|
| | | 10 μmol/l | 5 μmol/l | 2.5 μmol/l |
| (I-b) | 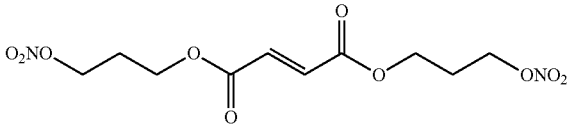<br>bis(3-(nitrooxy)propyl) fumarate | −99% | −96 | n.a. |
| (I-c) | 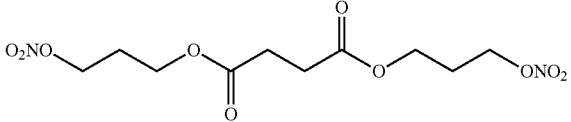<br>bis(3-(nitrooxy)propyl) succinate | −99 | n.a. | n.a. |
| Ref | <br>3-nitrooxypropanol | −99% | −86 | −32 |

*reduction versus substrate control

As can be retrieved from table 2, the dicarboxylic diesters according to the present invention are highly efficient methanogenese inhibitors, while exhibiting very low vapor pressures making them particularly storage stable.

The invention claimed is:

1. A dicarboxylic acid diester of formula (I):

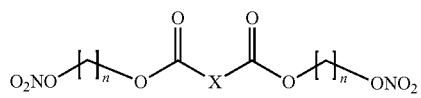

formula (I)

wherein
n is 3, and
X is a $C_1$ alkylene.

2. A process for the preparation of the dicarboxylic diester according to claim 1, wherein the process comprises a step of reacting a dicarboxylic acid of formula (II) with a nitrooxyalcohol of formula (III):

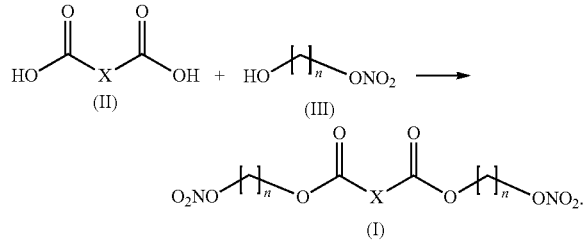

wherein n and X are as defined in claim 1.

3. A process for the preparation of the dicarboxylic diester according to claim 1, wherein the process comprises reacting a fatty acid of formula (II) with an alcohol of formula (IV) to obtain a fatty acid monoester of formula (V), followed by reacting the fatty acid monoester of formula (V) with nitrosulfuric acid:

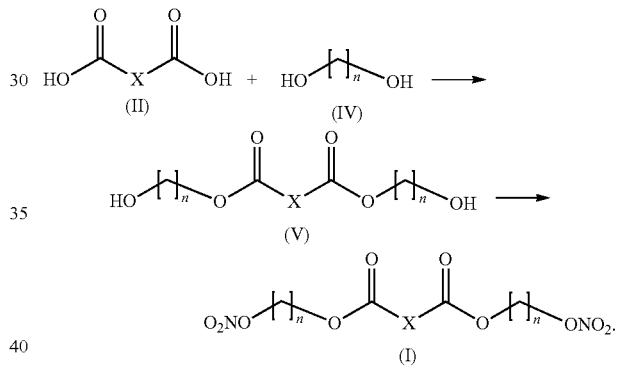

wherein n and X are as defined in claim 1.

4. A feed composition or feed additive comprising the dicarboxylic diester of formula (I) according to claim 1.

5. The feed composition according to claim 4, wherein the feed composition is a mineral premix, a vitamin premix, a premix comprising vitamins and minerals or a bolus.

6. A method for reducing the production of methane emanating from the digestive activities of ruminants and/or for improving ruminant animal performance comprising the oral administration of a sufficient amount of the dicarboxylic diester of formula (I) according to claim 1 to the animal.

7. The method according to claim 6, wherein the amount of the dicarboxylic diester of formula (I) administered to the ruminant animal is from 1 mg to 10 g per kg feed.

8. The method according to claim 6, wherein the methane production in ruminants is calculated in liters per kilogram of dry matter intake and wherein the amount of the dicarboxylic diester of formula (I) is administered to reduce the methane production of the ruminant animal by at least 10% when measured in metabolic chambers.

9. The method according to claim 6, wherein the ruminant animal is selected from the group consisting of cattle, goats, sheep, giraffes, American Bison, European bison, yaks, water buffalo, deer, camels, alpacas, llamas, wildebeest, antelope, pronghorn, and nilgai.

* * * * *